United States Patent [19]

Hayano et al.

[11] Patent Number: 5,473,426
[45] Date of Patent: Dec. 5, 1995

[54] DEFECT INSPECTION APPARATUS

[75] Inventors: Fuminori Hayano, Tokyo; Hitoshi Hamada, Kamagaya; Hideyuki Tashiro, Yokohama, all of Japan

[73] Assignee: Nikon Corporation, Tokyo, Japan

[21] Appl. No.: 427,738

[22] Filed: Apr. 24, 1995

Related U.S. Application Data

[63] Continuation of Ser. No. 328,347, Oct. 21, 1994, abandoned, which is a continuation-in-part of Ser. No. 204,968, Mar. 2, 1994, abandoned.

[30] Foreign Application Priority Data

Apr. 5, 1993 [JP] Japan ................................. 5-044912
Dec. 15, 1993 [JP] Japan ................................. 5-342269

[51] Int. Cl.$^6$ ................................................. G01N 21/89
[52] U.S. Cl. ...................... 356/237; 356/430; 250/237 R; 250/559.45
[58] Field of Search ........................ 356/237, 239, 356/338, 371, 445, 446, 394, 429–431; 359/739, 196, 227, 232, 558, 611, 738, 613; 250/237 R, 562, 563, 571, 572

[56] References Cited

U.S. PATENT DOCUMENTS

| | | | |
|---|---|---|---|
| 3,799,679 | 3/1974 | Simko | 356/237 |
| 4,160,913 | 7/1979 | Brenholdt | 356/431 |
| 4,988,204 | 1/1991 | Sakaguchi et al. | 356/237 |
| 5,072,128 | 12/1991 | Hayano et al. | 356/237 |

Primary Examiner—Hoa Q. Pham
Attorney, Agent, or Firm—Shapiro and Shapiro

[57] ABSTRACT

An apparatus includes a light source for emitting a light beam, a light beam expander for expanding the light beam in a predetermined direction, and radiating the expanded light beam onto an object to be inspected, a scanning device for moving the object to be inspected relative to the light beam to be radiated onto the object to be inspected, and a photodetector for photoelectrically converting scattered light generated from a defect (including foreign matter) on the object to be inspected, and inspects the defect on the basis of a photoelectric conversion signal obtained from the photodetector. A light-shielding plate having a plurality of edges for limiting the light beam expanded by the light beam expander at the two end portions, in the expansion direction, of the light beam is arranged, and at least one of the plurality of edges is formed to be transverse to the relative scanning direction (Y direction).

17 Claims, 9 Drawing Sheets

SCANNING DIRECTION

DEFECT INSPECTION APPARATUS

This is a continuation of application Ser. No. 08/328,347 filed Oct. 21, 1994, now abandoned, which is a continuation-in-part of application Ser. No. 08/204,968 filed Mar. 2, 1994 (abandoned).

BACKGROUND OF THE INVENTION

1. Field of the Invention

The present invention relates to a defect inspection apparatus and, more particularly, to an apparatus suitably used in inspection of defects such as foreign matter attached to the surface of a reticle or a photomask used as an original plate, or the surface of an anti-dust film (pellicle) of the original plate in the manufacture of, e.g., a semiconductor element in a photolithography process.

2. Related Background Art

In the manufacture of a semiconductor element, a liquid crystal display element, or the like in the photolithography process, an exposure apparatus for transferring a pattern formed on a reticle or a photomask (to be referred to as a "reticle" hereinafter) as an original plate onto a photosensitive substrate via a projection optical system is used. When foreign matter larger than a prescribed size becomes attached to the pattern formation surface or to a surface opposing the pattern formation surface of the reticle, or when a pattern on the pattern formation surface includes a defect, a pattern formed on the photosensitive substrate becomes defective. For this reason, before the reticle is attached to the exposure apparatus, the presence/absence of defects including foreign matter, the position of a defect, the size of a defect, and the like must be inspected.

In order to prevent foreign matter from becoming directly attached to the reticle, an anti-dust film called a pellicle is often formed on the two surfaces (or one surface) of the reticle. Even for a reticle formed with such pellicle, the presence/absence of defects including foreign matter, the position of a defect, the size of a defect, and the like on the surface of the pellicle must be inspected.

FIG. 5 shows an example of a conventional defect inspection apparatus. For the sake of explanation, a three-dimensional XYZ coordinate system is also illustrated in FIG. 5.

Referring to FIG. 5, a reticle 1 to be inspected is placed on a table 2 facing its pattern formation surface down. The table 2 is movable in the Y direction by a driving device 3. The moving amount, in the Y direction, of the table 2 is measured by a distance measuring device 4 such as a linear encoder. A light beam L1 emitted from a laser light source 5 is converted into a sheet-like light beam L2 expanded in the X direction via a negative cylindrical lens 6 and a positive cylindrical lens 7. The light beam L2 is radiated onto the surface of the reticle 1, and forms a slit-like illumination region 8 expanding in the X direction on an upper surface 1a of the reticle 1.

If a defect 9 such as foreign matter is present in the illumination region 8 on the upper surface 1a of the reticle 1, scattered light L3 is generated from the defect 9 upon radiation of the light beam L2. The scattered light L3 is focused by a light-receiving lens 10, and an image of the defect 9 is formed on the imaging surface of a one-dimensional image pickup element 11 such as a one-dimensional CCD. The one-dimensional image pickup element 11 has a plurality of light-receiving pixels, and each light-receiving pixel receives light from a predetermined position in the X direction. The coordinate in the X direction (X coordinate value) of the defect 9 on the reticle 1 can be determined on the basis of the position of the light-receiving pixel, which receives the image of the defect, of the one-dimensional image pickup element 11, and the coordinate in the Y direction (Y coordinate value) of the defect 9 can be determined on the basis of the distance measurement output from the distance measuring device 4 at that time. Furthermore, since the one-dimensional image pickup element 11 outputs a pixel output signal having a magnitude proportional to the received light amount, the size of the defect 9 can be roughly determined based on the magnitude of the pixel output signal.

Therefore, the inspection result can be displayed as, e.g., a table which shows the size of the defect in correspondence with the X and Y coordinate values of the defect, or can be displayed as a defect map on the display screen of a CRT display.

However, in the defect inspection apparatus shown in FIG. 5, when a defect on the upper surface (a surface opposing the formation surface of a circuit pattern) 1a of the reticle 1 is to be inspected, the light beam L2 is transmitted through the reticle 1, and is diffracted by a fine circuit pattern on a lower surface (the formation surface of the circuit pattern) 1b of the reticle 1. The diffracted light is focused by the light-receiving lens 10 as if it were scattered light from a defect, and is undesirably detected by the one-dimensional image pickup element 11.

FIG. 6 shows another example of a conventional defect inspection apparatus. For the sake of simplicity, a three-dimensional XYZ coordinate system is also illustrated in FIG. 6.

Referring to FIG. 6, a reticle 1 to be inspected is placed on a table (not shown) facing its pattern formation surface down. A light beam L4 emitted from a laser light source 12 is expanded in one direction by a negative cylindrical lens 13 and a focusing lens 14, thus generating a sheet-like light beam L5. The light beam L5 is obliquely radiated onto an upper surface 1a of the reticle 1 at an angle $\alpha$, and forms a slit-like illumination region 15 expanding in the X direction on the upper surface 1a of the reticle.

If a defect such as foreign matter is present in the illumination region 15 on the upper surface 1a of the reticle, scattered light is generated from the defect upon radiation of the light beam L5. The scattered light from the defect in the illumination region 15 is detected by a one-dimensional image pickup element 11 via a light-receiving lens 10.

In this case, when the radiation angle $\alpha$ of the light beam L5 with respect to the upper surface 1a of the reticle is set to be 5° or less, since the transmittance of the reticle 1 becomes considerably small, most of the incident light beam L5 is reflected, and does not reach a lower surface 1b of the reticle, on which a circuit pattern is formed. Therefore, the diffracted light amount from the circuit pattern decreases, and diffracted light from the circuit pattern can be prevented from being erroneously detected as scattered light from a defect on the reticle 1.

In the above-mentioned prior art, the laser light source 5 or 12 is used as a light source. Since the laser light source has a high luminance, even when the slit-like illumination region 8 or 15 is formed, the light amount per unit area (to be referred to as "illuminance" hereinafter) in the illumination region is large, and scattered light from a very small defect can be reliably detected.

However, a light beam emitted from the laser light source is called a Gaussian beam, i.e., the luminance level is highest at the center of the light beam, and is concentrically lowered toward the periphery. For this reason, in both the illuminance distributions of the illumination regions 8 and 15 shown in FIGS. 5 and 6, the luminance level is lowered toward the periphery.

FIG. 7A shows an illuminance distribution S(Y), in the Y direction, of a certain section of the illumination region 8 shown in FIG. 5, and FIG. 7B shows an illuminance distribution S(X), in the X direction, of the section of the illumination region 8 shown in FIG. 5. As shown in FIG. 7B, the illuminance levels at two end portions 8a and 8b in the X direction are considerably lower than that at the central portion. The same applies to the illuminance distribution of the illumination region 15 shown in FIG. 6.

In this case, when the moving speed of the table 2 by the driving device 3 in FIG. 5 is set to always detect scattered light based on a light beam component corresponding to the peak of the illuminance distribution in the Y direction shown in FIG. 7A, the light beam can always be radiated at an almost uniform illuminance level in the Y direction of the reticle 1.

However, in the X direction of the reticle 1, since the luminance level near the center of the reticle 1 is high, and the luminance levels at the two end portions 8a and 8b in the X direction are low, even if the defect size remains the same, the pixel output signal from the one-dimensional image pickup element 11 assumes a different value depending on the attached position, in the X direction, of the defect. Therefore, upon estimation of the defect size from the value of the pixel output signal, a large error may be generated depending on the attached position, in the X direction, of the defect.

In order to eliminate such a drawback, each pixel output signal is multiplied with the reciprocal number of an illuminance corresponding to the position in the X direction as a predetermined correction coefficient in accordance with the detected position, in the X direction, of the scattered light, i.e., the address (a numerical value indicating the position of the pixel) of the light-receiving pixel of the one-dimensional image pickup element 11, thus obtaining an output independently of the position in the X direction.

However, in the defect inspection apparatus shown in FIG. 6, when the height of the reticle 1 changes even slightly, the illuminance distribution with respect to the position in the X direction largely changes. For this reason, even when the above-mentioned correction method is adopted, a satisfactory correction effect cannot often be obtained.

More specifically, in the defect inspection apparatus shown in FIG. 6, since the light beam L5 is obliquely incident on the reticle 1 at the angle $\alpha$, if the height, in the Z direction, of the reticle 1, changes by $\Delta h$, the illuminance center (the position, in the X direction, on the reticle 1 where the maximum illuminance level is obtained) of the illumination region 15 on the reticle 1 is decentered by ($\Delta h/\tan\alpha$). For example, when $\alpha=5°$, if the surface of the reticle 1 is shifted by 1 mm in the Z direction, the illuminance center is shifted by 1 mm/tan5°, i.e., 11 mm. When the illuminance center of the illumination region 15 changes, the illuminance distribution, in the X direction, of the illumination region 15 also changes. In particular, the illuminance levels near the two ends, in the X direction, of the illumination region 15 change by several fractions to several times upon change in height of the reticle 1.

Therefore, when the height of the reticle 1 changes, and the illuminance center of the illumination region 15 is shifted, even if the pixel output signal from the one-dimensional image pickup element 11 is multiplied with a predetermined correction coefficient, nonuniformity, in the X direction, of defect detection sensitivity still remains.

The above-mentioned drawback is caused by an upward peak pattern (Gaussian distribution) of the illuminance distribution, in the X direction, of the illumination region 8 or 15 on the reticle 1, as shown in FIG. 7B, and can be eliminated by setting the illuminance distribution to have an almost uniform illuminance level independently of the position in the X direction.

As method of obtaining a uniform illuminance distribution, the enlargement magnifications of the lenses 6 and 7 in FIG. 5 and the lenses 13 and 14 in FIG. 6 are increased, so that only the central portion of the Gaussian distribution is used.

However, if a light beam is simply expanded and is radiated onto the reticle 1, the light beam is also radiated onto portions near side surfaces 1c and 1d of the reticle 1 and the table 2, strong scattered light is generated from these radiated portions, and such scattered light cannot be distinguished from that from a defect. Thus, as still another countermeasure, the two end portions of an expanded light beam may be shielded by a light-shielding plate.

FIG. 8 shows main part of an apparatus in which such a countermeasure is taken in the apparatus shown in FIG. 5. Note that a three-dimensional XYZ coordinate system is also illustrated in FIG. 8 for the sake of explanation. Referring to FIG. 8, a light beam L1 emitted from a laser light source 5 and having a Gaussian distribution is expanded in the X direction by a negative cylindrical lens 6A and a positive cylindrical lens 7A, thus forming a light beam L6. The light beam L6 is radiated onto a light-shielding plate 16 formed with a rectangular opening 17, which is elongated in the X direction. A light beam L7 obtained by shielding the two end portions, in the X direction, of the light beam L6 by the light-shielding plate 16 is radiated onto the reticle 1, and forms a slit-like illumination region 18 expanding in the X direction on the reticle 1. Thus, illuminance nonuniformity, in the X direction, in the illumination region 18 on the reticle 1 can be eliminated, a light beam can be prevented from being radiated onto portions near the side surfaces 1c and 1d of the reticle 1, and no unnecessary scattered light is generated.

However, when the light beam L6 is limited by the light-shielding plate 16, as shown in FIG. 8, a diffraction effect when the light beam L6 passes through the rectangular opening 17 poses a problem. Assume that, following the general convention, the width of the Gaussian beam is defined by a width corresponding to a point where the illuminance becomes 13.5% of the maximum illuminance, the width, in the X direction, of the light beam L6 is represented by $\Delta X$, and the width, in the Y direction, of the beam L6 is represented by $\Delta Y$. Furthermore, assuming that the length, in the X direction (the length in the longitudinal direction), of the rectangular opening 17 of the light-shielding plate 16 is represented by a, and the width in the Y direction is represented by b, the following relations are satisfied:

$$\Delta X \gg a \quad (1)$$

$$\Delta Y \ll b \quad (2)$$

Therefore, no diffraction occurs in the Y direction in the opening 17, and diffraction occurs in only the X direction. For this reason, as is apparent from the diffraction theory, even when the width, in the X direction, of the slit-like illumination region 18 is almost a, the illuminance distribution S(X), in the X direction, in the illuminance region 18 has a fine structure, as shown in FIG. 9.

As shown in FIG. 9, the illuminance distribution S(X), in the X direction, in the illumination region 18 largely changes in a sine-wave pattern at especially two end portions, and has valleys corresponding to extremely low illuminance levels at positions 18a and 18b in the X direction. Therefore, even when the reticle 1 is moved in the Y direction, the illuminance of the light beam is always lowered at the positions 18a and 18b in FIG. 9, and defect detection sensitivity is impaired as compared to that for other regions.

SUMMARY OF THE INVENTION

The present invention has been made in consideration of the above situation, and has as its object to provide a defect inspection apparatus for inspecting a defect by radiating a slit-like light beam onto an object to be inspected, and receiving scattered light from a defect on the object to be inspected, wherein the light beam can be prevented from being radiated onto portions other than a region to be inspected on the object to be inspected, and a variation in defect detection sensitivity caused by a variation in illumination distribution in the slit-like illumination region can be avoided.

In order to achieve the above object, as shown in, e.g., FIGS. 1A and 1B, there is provided a defect inspection apparatus according to the present invention which comprises a light source (5) for emitting a light beam, light beam expansion means (6A, 7A) for expanding the light beam in a predetermined direction, and radiating the expanded light beam onto an object (1) to be inspected, scanning means (2, 3) for scanning the light beam to be radiated onto the object (1) to be inspected relative to the object (1) to be inspected (i.e., relatively moving them), and light-receiving means (10, 11) for photoelectrically converting scattered light generated from a defect (including foreign matter) on the object (1) to be inspected, and which inspects the defect on the basis of a photoelectric conversion signal obtained from the light-receiving means, wherein the apparatus further comprises light-shielding means (16) having a plurality of edges (19a, 19b) for limiting the light beam (L6) expanded by the light beam expansion means at two end portions, in 10 an expansion direction (X direction) of the light beam (L6), and at least one of the plurality of edges is formed to be transverse to the relative scanning direction (Y direction).

As an example of the defect inspection apparatus according to the present invention, the light-shielding means (16) may comprise an edge 19a for limiting one end portion, in the expansion direction (X direction), of the light beam (L6), and an edge 19b for limiting the other end portion thereof, and the edges 19a and 19b may be formed to be substantially parallel to each other.

According to the present invention with the above-mentioned arrangement, a light beam (L1) emitted from the light source (5) and having a Gaussian distribution is expanded in a predetermined direction (defined to be the X direction) by the light beam expansion means (6A, 7A), thus forming a light beam (L6). The light beam (L6) is radiated onto an opening (19) of the light-shielding means (16), and its width in the X direction is limited by the plurality of edges of the opening (19). A light beam (L8) passing through the opening (19) is radiated onto the object (1) to be inspected, and forms a slit-like illumination region (20) expanding in the X direction on the object (1) to be inspected. The object (1) to be inspected can be moved by the scanning means (2, 3) in the Y direction relative to the light beam (L8).

FIG. 1B is a view in the XY plane obtained when the light beam (L6) incident on the opening (19) is viewed from the light source (5) side. Referring to FIG. 1B, the left edge (19a) and the right edge (19b) of the opening (19) are respectively inclined at almost 45° with respect to the Y axis as the scanning direction. When the light beam (L6) passes through the opening (19), since the edges (19a, 19b) shield the light beam (L6), a diffraction effect occurs by only these two edges, and illuminance nonuniformity due to the diffraction effect is generated in the direction parallel to the edges (19a, 19b). FIGS. 2A and 2B show this state.

FIGS. 2A and 2B show a simplified illuminance distribution in the illumination region (20) formed by the light beam (L8) via the opening (19) on the object (1) to be inspected. FIG. 2A shows, so to speak, equi-illuminance lines obtained by connecting the same illuminance level portions in the illumination region (20) by solid curves. As can be seen from FIG. 2A, fringes of illuminance nonuniformity appear in the direction parallel to the edges (19a, 19b) of the opening (19) (in the direction crossing the Y axis at 45°) due to the diffraction effect. An illuminance distribution in the X direction obtained when the illumination region (20) is cut along a line PP' parallel to the X axis corresponds to a distribution SP indicated by a solid curve in FIG. 2B. Similarly, an illuminance distribution in the X direction obtained when the illumination region (20) is cut along a line QQ' parallel to the X axis corresponds to a distribution SQ indicated by a broken curve in FIG. 2B. As can be understood from a comparison between the distributions SP and SQ in FIG. 2B, an illuminance level at, e.g., a position X1 as a valley in the distribution SP corresponds to a peak in the distribution SQ.

More specifically, when the object (1) is moved in the Y direction relative to the light beam (L8), the illuminance level at the position X1 in the X direction changes in accordance with the relative moving amount in the Y direction, but always has a valley and a peak. In other words, the illuminance level is high at some point although it is low at some other point. Therefore, when the object (1) is scanned relative to the light beam (L8), an almost uniform illuminance distribution can be obtained on the surface to be inspected of the object (1) to be inspected, and defect detection sensitivity can also be uniformed.

When the light-shielding means (16) has the edge (19a) for limiting one end portion, in the expansion direction (X direction), of the light beam (L6), and the edge (19b) for limiting the other end portion thereof, and the edges (19a, 19b) are formed to be substantially parallel to each other, the manufacture of the light-shielding means (16) is easy, and fringes of illuminance nonuniformity caused by the edge (19a) are formed to be parallel to those of illuminance nonuniformity caused by the edge (19b), thus uniforming the illuminance distribution on the surface to be inspected more effectively. Note that the defect inspection apparatus according to the present invention is preferably designed to perform inspection on the object (21) to be inspected on the basis of the received light intensity distribution of scattered light, which has been detected for a predetermined time period by light-receiving means (17 to 20), as shown in, e.g., FIG. 10. The predetermined time period is preferably defined to be a time required for the received light intensity distribution of scattered light to change by almost one cycle.

BRIEF DESCRIPTION OF THE DRAWINGS

FIGS. 11A to 11C are views for explaining oblique diffraction fringes on a radiation region formed by partial light-shielding according to the embodiment shown in FIG. 10, in which FIG. 11A shows a partial light-shielding opening, FIG. 11B shows a pattern of oblique diffraction fringes, and FIG. 11C shows the intensity distribution of radiated light;

DESCRIPTION OF THE PREFERRED EMBODIMENTS

Figure 8:
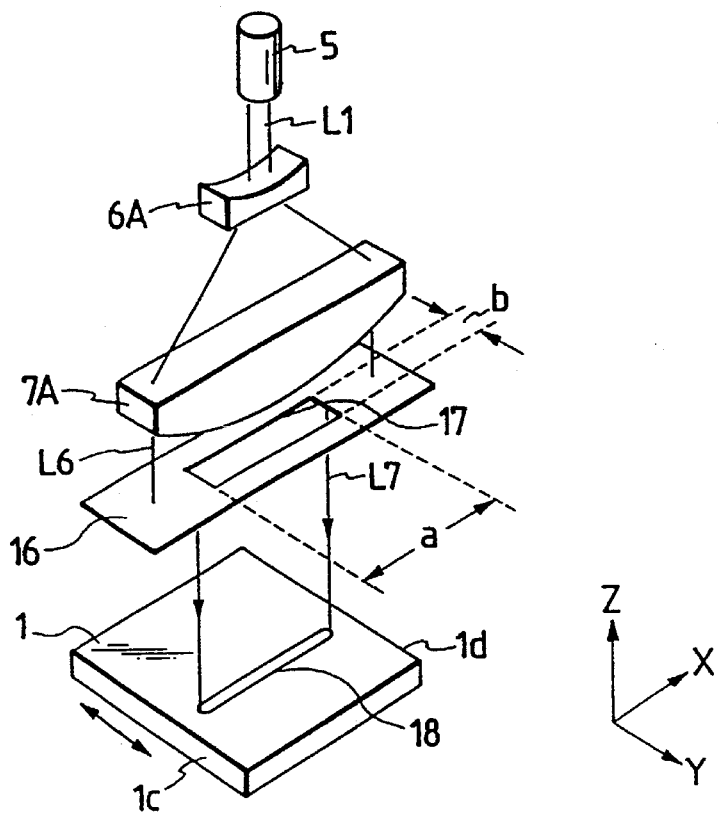
FIG. 8 is a perspective view showing a case wherein a light beam is expanded, and the expanded beam is limited by a light-shielding plate in the defect inspection apparatus shown in FIG. 6.
Figure 9:
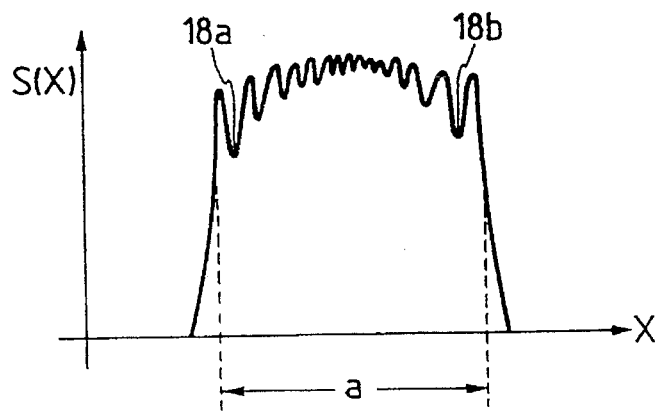
FIG. 9 is a graph showing the illuminance distribution, in the X direction, of an illumination region on a reticle shown in FIG. 8.

An embodiment of a defect inspection apparatus according to the present invention will be described below with reference to FIGS. 1A to 4C. In this embodiment, the shape of the opening in the light-shielding plate 16 of the apparatus shown in FIG. 8 is improved. Thus, the same reference numerals as in FIGS. 1A and 1B denote corresponding portions in FIGS. 5 and 8, and a detailed description thereof will be omitted. For the sake of explanation, a three-dimensional XYZ coordinate system or a two-dimensional XY coordinate system is illustrated in the drawings.

Figure 1A:
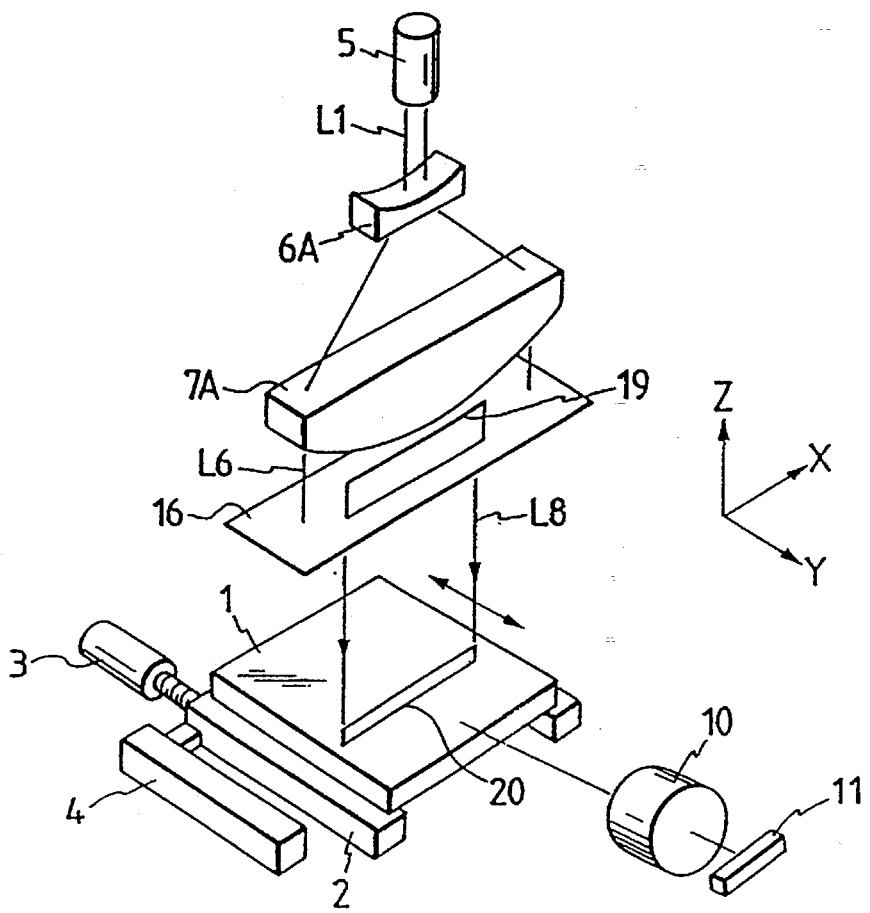
FIG. 1A is a perspective view showing an embodiment of a defect inspection apparatus according to the present invention.

FIG. 1A shows the arrangement of a defect inspection apparatus according to this embodiment. Referring to FIG. 1A, a reticle 1 as an object to be inspected is placed on a table 2, and the table 2 is moved in the Y direction by a driving device 3. The moving amount, in the Y direction, of the table 2 is measured by a distance measuring device 4. A light beam L1 emitted from a laser light source 5 is converted into a sheet-like light beam L6 expanded in almost the X direction via a negative cylindrical lens 6A and a positive cylindrical lens 7A. The light beam 6A is radiated onto a parallelogrammic opening 19 of a light-shielding plate 16. A light beam L8 passing through the opening 19 is radiated onto the surface of the reticle 1, and forms a slit-like illumination region 20 expanding in almost the X direction on the surface of the reticle 1. Scattered light from a defect including foreign matter in the illumination region 20 is focused by a light-receiving lens 10, and an image of the defect is formed on the imaging surface of a one-dimensional image pickup element 11.

Figure 1B:
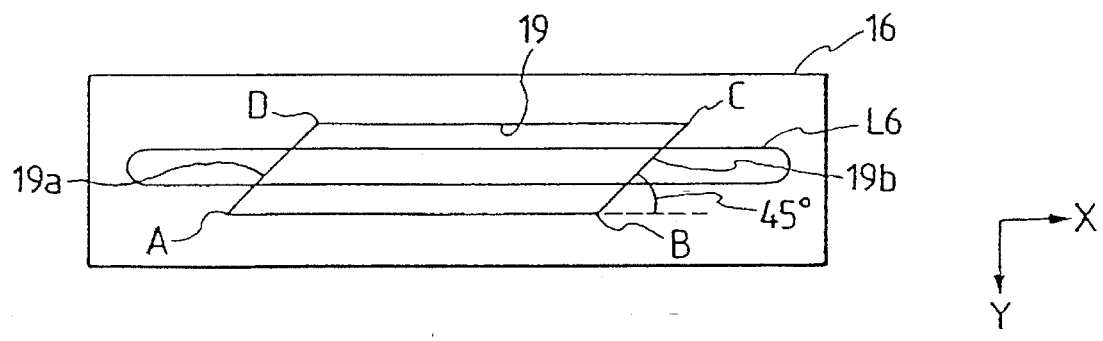
FIG. 1B is a plan view showing a light-shielding plate 16 in FIG. 1A.

FIG. 1B is a plan view obtained when the light-shielding plate 16 of this embodiment is viewed from the light source 5 side. As shown in FIG. 1B, if the four vertices of the parallelogrammic opening 19 formed on the light-shielding plate 16 are represented by A, B, C, and D, an edge 19a defined by the side AD is parallel to an edge 19b defined by the side BC. The edges 19a (side AB) and 19b (side BC) cross the Y direction as the relative scanning direction at 45°, and the sides DC and AB are parallel to the X direction. The two end portions, in the X direction, of the light beam L6 are limited by the edges 19a and 19b of the opening 19. Since the interval between the sides AB and DC of the opening 19 is larger than the width, in the Y direction, of the light beam L6, the light beam L6 is not limited by the sides AB and DC of the opening 19.

Therefore, on the slit-like illumination region 20 in FIG. 1A, a diffraction pattern (fringes of illuminance nonuniformity) is formed in the direction parallel to the edges 19a and 19b due to the diffraction effect of the opening 19.

Figure 2A:
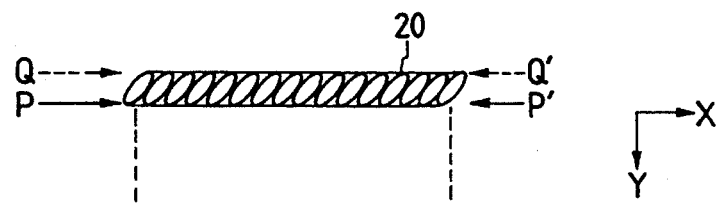
FIG. 2A is a view showing a kind of equi-illuminance lines of the illuminance distribution of the illumination region on a reticle in FIG. 1A.
Figure 2B:
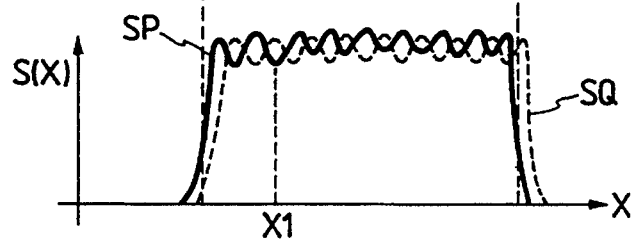
FIG. 2B is a graph showing the illuminance distributions, in the X direction, of two sections of the illuminance distribution shown in FIG. 2A.

FIGS. 2A and 2B show the illuminance distribution of the light beam L8 on the illumination region 20 on the reticle 1 under the diffraction effect of the parallelogrammic opening 19 in FIG. 1B.

Figure 3A:
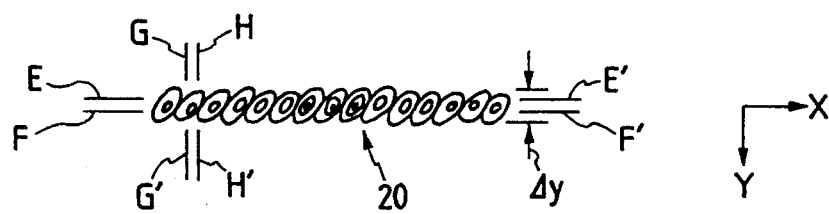
FIG. 3A is a view showing a kind of more detailed equi-illuminance lines of the illuminance distribution of the illumination region on the reticle in FIG. 1A.
Figure 3B:
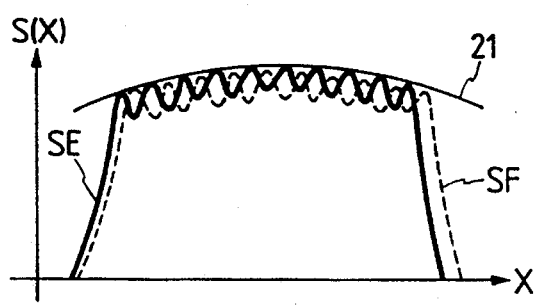
FIG. 3B is a graph showing the illuminance distributions, in the X direction, of two sections of the illuminance distribution shown in FIG. 3A.
Figure 3C:
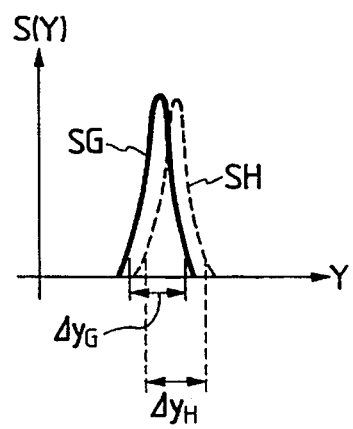
FIG. 3C is a graph showing the illuminance distributions, in the Y direction, of two sections of the illuminance distribution shown in FIG. 3A.

FIGS. 3A to 3C show in more detail the structure of the illuminance distribution of the light beam L8 on the illumination region 20 shown in FIGS. 2A and 2B. FIG. 3A shows a kind of equi-illuminance lines obtained by connecting the same illuminance level portions in the illumination region 20 by solid curves. Illuminance distributions S(X) in the X direction obtained when the illuminance distribution shown in FIG. 3A is cut along lines EE' and FF' parallel to the X axis respectively correspond to a distribution SE indicated by a solid curve in FIG. 3B and a distribution SF indicated by a broken curve in FIG. 3B. Also, illuminance distributions S(Y) in the Y direction obtained when the illuminance distribution shown in FIG. 3A is cut along lines GG' and HH' parallel to the Y axis respectively correspond to a distribution SG indicated by a solid curve in FIG. 3C and a distribution SH indicated by a broken curve in FIG. 3C.

In this case, when the table 2 in FIG. 1A is moved in the Y direction, since an arbitrary point on the reticle 1 is illuminated with the illuminance distributions SE and SF shown in FIG. 3B, the illuminance distribution on the entire surface of the reticle 1 becomes almost uniform when these distributions are temporally integrated. Therefore, defect detection sensitivity on the entire surface of the reticle 1 is also almost uniform.

Figure 6:
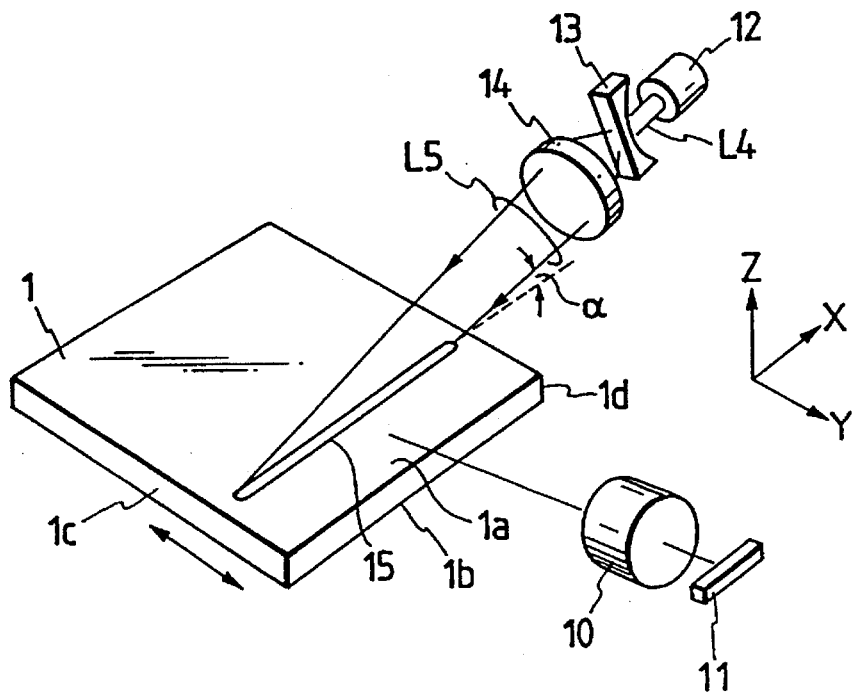
FIG. 6 is a perspective view showing another example of a conventional defect inspection apparatus.
Figure 7A:
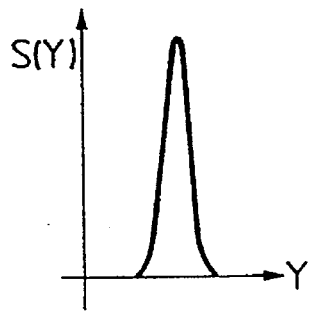
FIG. 7A is a graph showing the illuminance distribution, in the Y direction, of an illumination region 8 in FIG. 5.
Figure 7B:
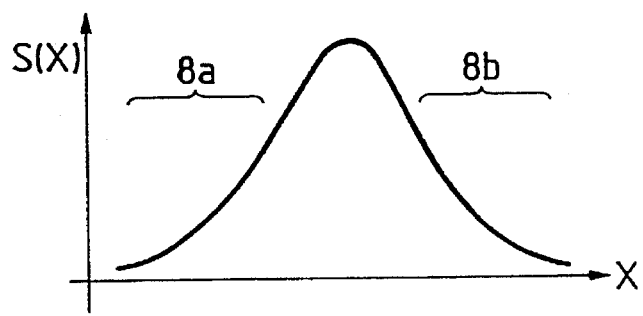
FIG. 7B is a graph showing the illuminance distribution, is the X direction, of the illumination region 8 in FIG. 5.

Of course, when the light-shielding plate 16 having the opening 19 is applied to the conventional apparatus having an oblique incidence system shown in FIG. 6, a change in detection sensitivity becomes considerably small even when the height of the reticle 1 changes.

As indicated by an envelope 21 in the illuminance distribution shown in FIG. 3B, even when a laser beam having a Gaussian distribution is expanded and is radiated via the opening, illuminance nonuniformity inevitably remains to some extent.

In this embodiment, illuminance nonuniformity in the X direction, which still remains, as indicated by the envelope 21 in FIG. 3B, is corrected by multiplying pixel output signals from the one-dimensional image pickup element 11 in FIG. 1A with different correction coefficients in correspondence with the addresses of light-receiving pixels. More specifically, the reciprocal number of an illuminance level corresponding to the address of each light-receiving pixel of the one-dimensional image pickup element 11, which illuminance level is obtained from the envelope 21 shown in FIG. 3B, can be used as a gain of an amplifier for receiving each pixel output signal.

The moving speed upon movement of the reticle 1 in the Y direction can be set, so that a peak portion of the illuminance distribution in the illumination region 20 is always irradiated upon detection of the intensity of scattered light at an arbitrary position, in the X direction, on the reticle 1.

More specifically, since the illuminance distribution of the light beam in the illumination region 20 has a periodically two-dimensional distribution in an oblique direction, as shown in FIG. 3A, a width $\Delta y_G$, in the Y direction, of the distribution SG shown in FIG. 3C, and a width $\Delta y_H$, in the Y direction, of the distribution SH (each of these widths is smaller than $\Delta y$) shown in FIG. 3C are assumed to be beam widths in the Y direction. Under this assumption, when the reticle 1 is fed in the Y direction by a step amount of $\min(\Delta y_g(X))/4$ or less or $\min(\Delta y_H(X))/4$ or less ($\min(\Delta y_G(X))$ or $\min(\Delta y_H(X))$ is the minimum value of the width $\Delta y_G$ or $\Delta y_H$ at an arbitrary position, in the X direction, on the reticle 1), the peak portion of the illuminance distribution in the illumination region 20 is radiated upon detection of the intensity of scattered light at the arbitrary position, in the X direction, on the reticle 1.

More specifically, in the defect inspection apparatus using the light-shielding plate 16 on which the deformed opening 19 is formed, like in this embodiment, the two-dimensional illuminance nonuniformity on the reticle 1 in the X and Y directions is determined by the shape of the opening in the light-shielding plate 16 and the moving speed (the relative speed in the Y direction between the reticle 1 and the light beam).

As for the processing of a pixel output signal from the one-dimensional image pickup element 11 in FIG. 1A, since the illuminance level of a light beam on a defect changes upon movement of the reticle 1 in the Y direction, and the value of a pixel output signal corresponding to the defect also changes, the maximum value of the pixel output signal is extracted. More specifically, when the value of the pixel output signal from the one-dimensional image pickup element 11 obtained when the illuminance distribution indicated by the line FF' in FIG. 3A is located on the defect is larger that obtained when the illuminance distribution indicated by the line EE' in FIG. 3A is located on the defect, the larger value, the address of the light-receiving element of the one-dimensional image pickup element 11 at that time, and the distance measurement output from the distance measuring device 4 are stored as data in a storage unit such as a memory.

Modifications of the opening formed in the light-shielding plate 16 in FIG. 1B will be described below with reference to FIGS. 4A to 4C.

Figure 4A:
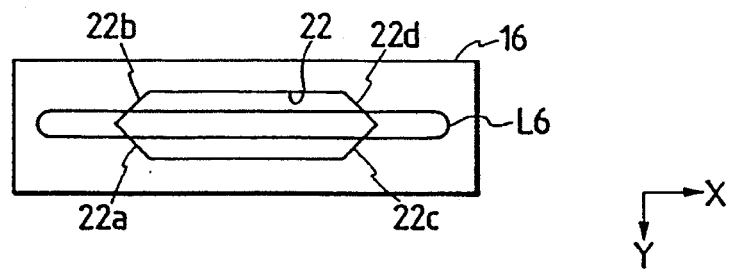
FIGS. 4A to 4C are plan views showing modifications of an opening formed on the light-shielding plates according to the embodiment shown in FIG. 1A.
Figure 5:
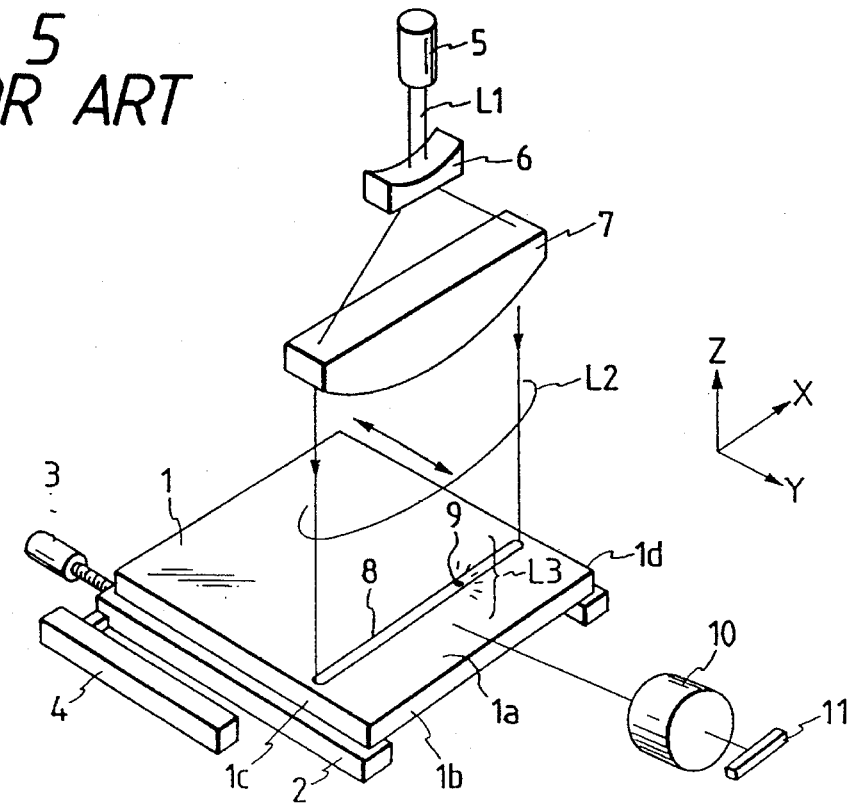
FIG. 5 is a perspective view showing an example of a conventional defect inspection apparatus.

FIG. 4A shows a case wherein a hexagonal opening 22 is formed in the light-shielding plate 16. Referring to FIG. 4A, the light beam L6 emerging from the cylindrical lens 7A in FIG. 1A is radiated onto the opening 22. Two left edges 22a and 22b, in the X direction, of the opening 22 cross the Y direction at almost 45°, and are perpendicular to each other. Similarly, two right edges 22c and 22d of the opening 22 cross the Y direction at almost 45°, and are perpendicular to each other. These edges 22a, 22b, 22c, and 22d limit the width, in the X direction, of the light beam L6. The light beam L6 is diffracted by these oblique edges 22a, 22b, 22c, and 22d, and is radiated onto the reticle as light having a two-dimensional illuminance distribution in a checkerboard pattern. Therefore, when the reticle is moved in the Y direction, illuminance nonuniformity of the light beam in the X direction can be eliminated, as in the case of the opening shown in FIG. 1B.

Figure 4B:
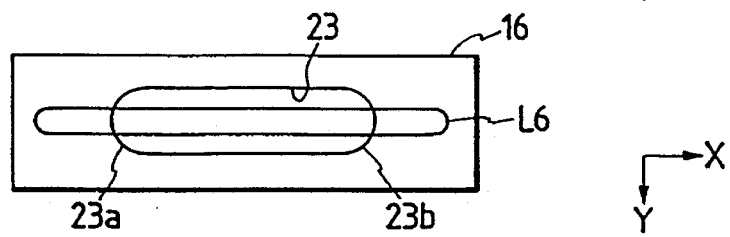

FIG. 4B shows a case wherein an opening 23 having two arcuated end portions is formed in the light-shielding plate 16. Referring to FIG. 4B, the two end portions, in the X direction, of the opening 23 respectively have arcuated edges 23a and 23b. Therefore, the light beam L6 is diffracted by these arcuated edges 23a and 23b, and is radiated onto the reticle as light having a two-dimensional illuminance distribution in a concentric pattern. Therefore, when the reticle is moved in the Y direction, illuminance nonuniformity of the light beam in the X direction can be eliminated, as in the case of the opening shown in FIG. 1B.

Figure 4C:
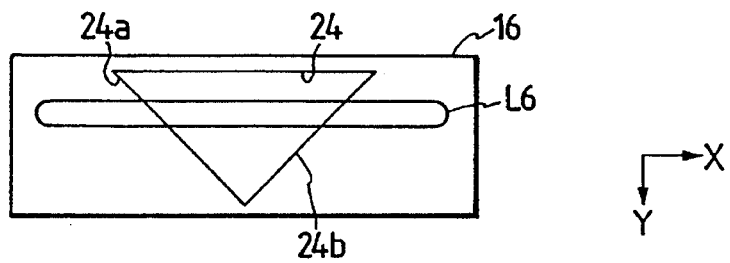

FIG. 4C shows a case wherein an isosceles-triangular opening 24 is formed in the light-shielding plate 16. Referring to FIG. 4C, the light beam L6 emerging from the cylindrical lens 7A in FIG. 1A is radiated onto the opening 24. A left edge 24a and a right edge 24b, in the X direction, of the opening 24 cross the Y direction at almost 45°, and are line-symmetrical with each other about the Y direction. These edges 24a and 24b limit the width, in the X direction, of the light beam L6. The light beam L6 is diffracted by these oblique edges 24a and 24b, and is radiated onto the reticle as light having a two-dimensional illumination distribution in a rhombic pattern. Therefore, when the reticle is moved in the Y direction, illuminance nonuniformity of the light beam in the X direction can be eliminated, as in the case of the opening shown in FIG. 1B.

In the above-mentioned embodiment, the present invention is applied to a case wherein a light beam is almost perpendicularly incident on an object to be inspected. However, the present invention can be applied to an apparatus having an oblique incidence system shown in FIG. 6, as a matter of course.

When the present invention is applied to the apparatus having the oblique incidence system shown in FIG. 6, since a light beam having microscopically two-dimensional illuminance nonuniformity is radiated onto the reticle. For this reason, when the reticle is moved at a predetermined speed relative to the light beam, defect detection sensitivity on the entire surface of the reticle can be uniformed.

The present invention is not limited to defect inspection on the reticle, but can be applied to defect inspection of, e.g., a pellicle formed on the reticle.

Another embodiment of the present invention will be described below with reference to FIGS. 10 to 13.

Figure 10:
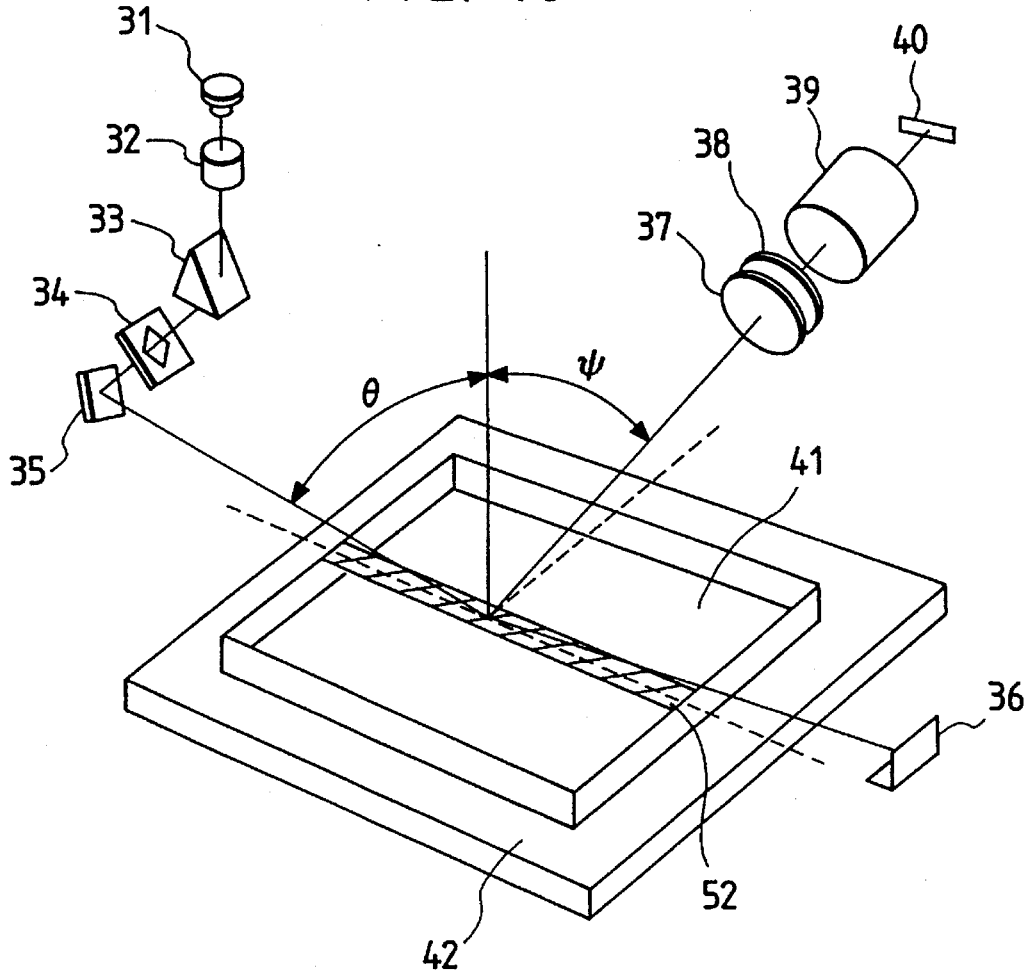
FIG. 10 is a perspective view for explaining the arrangement of a defect inspection apparatus according to another embodiment of the present invention.
Figure 10:
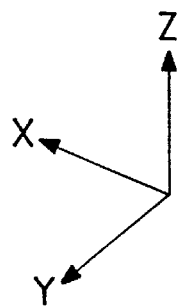

FIG. 10 is a perspective view for explaining the arrangement of a defect inspection apparatus according to another embodiment of the present invention.

Referring to FIG. 10, a laser beam emitted from a semiconductor laser 31 is converted into a collimated beam via a collimator lens 32, and the collimated beam is incident on an anamorphic prism 33. The laser beam incident on the anamorphic prism is expanded in the X direction in FIG. 10 to be converted into a light beam having an elliptic section, and the converted beam is incident on a diaphragm 34. In this case, the light intensity of the elliptic light beam, which has reached the diaphragm 34, exhibits a Gaussian distribution slower than that of the collimated beam obtained via the collimator lens 32.

Figure 11A:
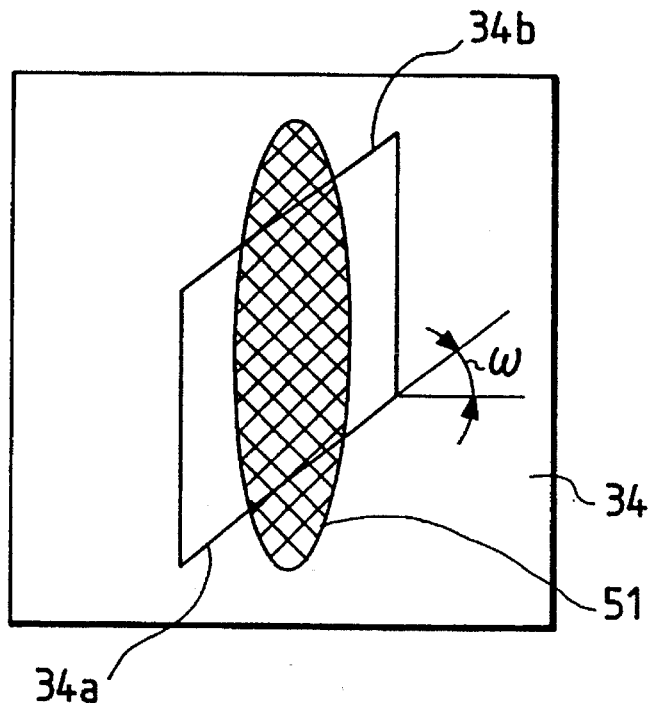

The diaphragm 34 partially shields an elliptic light beam 51 in the longitudinal direction thereof by a pair of edges 34a and 34b of its parallelepiped opening portion, as shown in FIG. 11A (as a result, the light intensity of the elliptic light beam 51 obtained via the diaphragm 34 becomes almost uniform in the longitudinal direction of the light beam).

The light beam passing through the diaphragm 34 is reflected by a mirror 35, and is incident on a pellicle 41 as a surface to be inspected to have an incident angle θ near 90°. The pellicle 41 is attached to a mask 42 via a frame, and extends in a direction almost parallel to the X-Y plane in FIG. 10. The mask 42 with the pellicle is placed on a table (not shown) as in the first embodiment in FIG. 1, and this table is movable by a driving device in the Y direction in FIG. 10.

The light beam incident on the surface of the pellicle 41 in a direction almost parallel thereto forms a band-shaped radiation region 52 extending along the X direction on the surface of the pellicle 41.

Regularly reflected light from the pellicle 41 is directly absorbed by a light absorbing member 36. On the other hand, scattered light on a foreign matter on the pellicle 41 is received by a light-receiving system arranged along the Y direction to have a light-receiving angle Ψ near 90°.

In the light-receiving system, the scattered light from the foreign matter is received by an image sensor 40 via a soft filter 37, a sharp cut filter 38, and a light-receiving lens 39. On the image sensor 40, nonsensitive bands are periodically arranged. Therefore, in order to prevent the scattered light from the foreign matter from being imaged on the nonsensitive bands on the image sensor 40 via the light-receiving lens 39, the imaging spot size is increased by the soft filter 37. In order to shield disturbance light which has a wavelength below that of visible light, and forms noise in a so-called scattered signal corresponding to the light intensity of the scattered light, the sharp cut filter 38 is arranged.

Processing of a scattered signal according to this embodiment will be described below with reference to FIGS. 11A to 11C and FIG. 12.

Figure 11B:
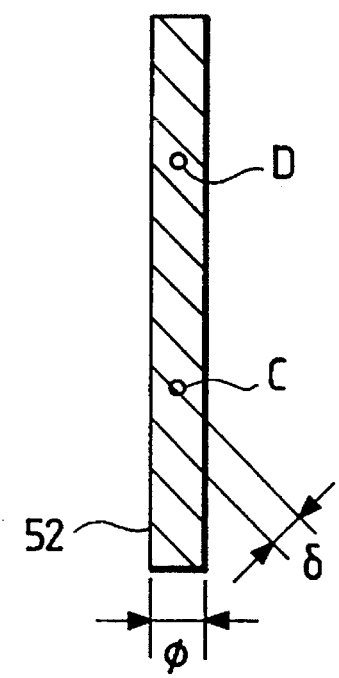

In this embodiment, as shown in FIG. 11B, radiated light intensity nonuniformity (a periodic change in light intensity of radiated light along the longitudinal direction of the band-shaped radiation region) due to a diffraction effect is formed in an oblique fringe pattern having an angle with respect to the scanning direction on the band-shaped radiation region 52 on the pellicle 41. More specifically, oblique diffraction fringes which are oblique with respect to the scanning direction are formed on the band-shaped radiation region 52 at an almost constant pitch.

In general, since a laser beam exhibits a Gaussian intensity distribution, it also exhibits Gaussian distributions in its longitudinal direction and a transverse direction thereto (a direction transverse to the longitudinal direction) even when the laser beam is expanded in a predetermined direction. In this embodiment, since the light beam is expanded in the predetermined direction, the Gaussian distribution in the longitudinal direction becomes very slow. Since the central region of the beam which is partially shielded in its longitudinal direction is utilized, the intensity of the radiated light on the band-shaped radiation region 52 is almost uniform in the longitudinal direction thereof. When the light beam is not partially shielded in the direction transverse to the longitudinal direction, the intensity of the radiated light on the band-shaped radiation region exhibits a Gaussian distribution in the direction transverse to the longitudinal direction, i.e., in the scanning direction.

However, a change in radiation light along the scanning direction always occurs with respect to respective foreign matters under the same condition during scanning. Furthermore, the size of a foreign matter, which poses a problem associated with the detection sensitivity, is considerably smaller than the width of the band-shaped radiation region, and scattered light can be received on a region where the intensity of the radiated light is almost constant in the scanning direction. Therefore, in the following description, the Gaussian distribution, in the direction transverse to the longitudinal direction, of the radiated light is ignored, and the intensity distribution, in the longitudinal direction, of the radiated light is assumed to be constant.

On the other hand, radiated light intensity nonuniformity due to the diffraction effect, i.e., a periodic change in light intensity of the radiated light along the longitudinal direction of the band-shaped radiation region is locally small on the beam central region, and it can be regarded that the light intensity on the beam central region is almost uniform as a whole. In practice, the detection sensitivity is influenced by a change in radiated light intensity due to diffraction on the peripheral portion, in the longitudinal direction, of the elliptic light beam 51.

Figure 11C:
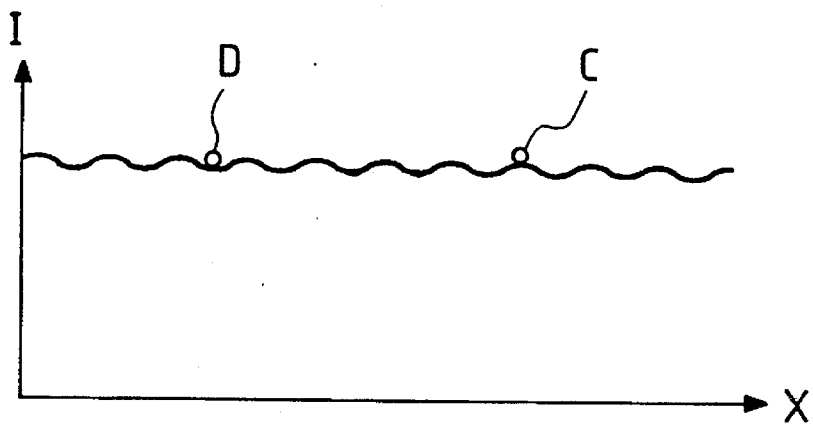

FIG. 11C shows the intensity distribution of the radiated light along the longitudinal direction of the band-shaped radiation region 52. In FIG. 11C, the ordinate represents the radiated light intensity, and the abscissa represents the longitudinal direction of the band-shaped radiation region 52.

As shown in FIG. 11C, the change in intensity of the radiated light due to diffraction is almost uniform and is periodic. In other words, a pitch δ of oblique diffraction fringes on the radiation region is almost constant, and the light intensities at upper and lower peak portions of the oblique diffraction fringes are respectively almost constant. For the purpose of easy understanding of the drawing, FIG. 11B illustrates the pitch δ of the oblique diffraction fringes to be larger than the actual one. However, in practice, the pitch δ is considerably smaller than a width Ω of the band-shaped radiation region.

As shown in FIGS. 11B and 11C, at a given instance to, assume that a foreign matter C is located on an upper peak portion of an oblique diffraction fringe (i.e., a portion corresponding to an almost maximal radiated light intensity), and a foreign matter D is located on a lower peak portion of an oblique diffraction fringe (i.e., a portion corresponding to an almost minimal radiated light intensity).

Figure 12:
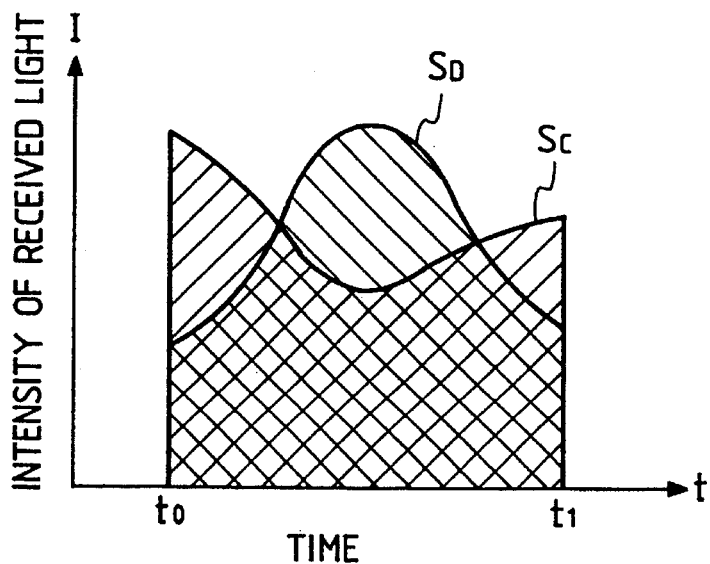
FIG. 12 is a graph for explaining the received light intensity distribution in the apparatus of the embodiment shown in FIG. 10.

FIG. 12 shows a state wherein the received light intensities of scattered light components from the two foreign matters present in the radiation region shown in FIGS. 11A to 11C change as the scanning progresses. In FIG. 12, the ordinate represents the intensity of received light, and the abscissa represents time.

In general, since the intensity of scattered light from a foreign matter is proportional to the intensity of radiated light, at the instance t0 in FIG. 12, the received light intensity of scattered light from the foreign matter C is almost maximal, and the received light intensity of scattered light from the foreign matter D is almost minimal.

Paying attention to the change in received light intensity of scattered light from the foreign matter C, the received light intensity, which is maximal at the instance t0, gradually decreases, becomes almost minimal, and then begins to increase. Thereafter, the received light intensity becomes almost maximal again at an instance t1. On the other hand, paying attention to the change in received light intensity of scattered light from the foreign matter D, the received light intensity, which is minimal at the instance t0, gradually increases, becomes almost maximal, and then begins to decrease. Thereafter, the received light intensity becomes almost minimal again at the instance t1.

As described above, during the time period from the instance t0 to the instance t1, the received light intensity distributions of the scattered light components from the foreign matters C and D on the radiation region change by almost one cycle. In other words, if the foreign matters C and D have the same size, a total accumulated received light amount $S_C$ from the foreign matter C and a total accumulated received light amount $S_D$ from the foreign matter D during the time period, in which the received light intensity distributions of the scattered light components change by almost one cycle, become almost equal to each other.

Therefore, in this embodiment, defect inspection (foreign matter inspection) is performed on the basis of a scattered signal obtained during the predetermined time period from the instance t0 to the instance t1. More specifically, defect inspection is performed on the basis of the received light intensity distribution of scattered light, which has been detected for a time period which is required for the received light intensity distribution from a foreign matter to change by almost one cycle. In this manner, according to this embodiment, radiation light components having almost the same accumulated light amount can be radiated onto respective foreign matters independently of the attached positions of the foreign matters. In addition, if the foreign matters have the same size, scattered light components having almost the same accumulated light amounts can be received.

Figure 13:
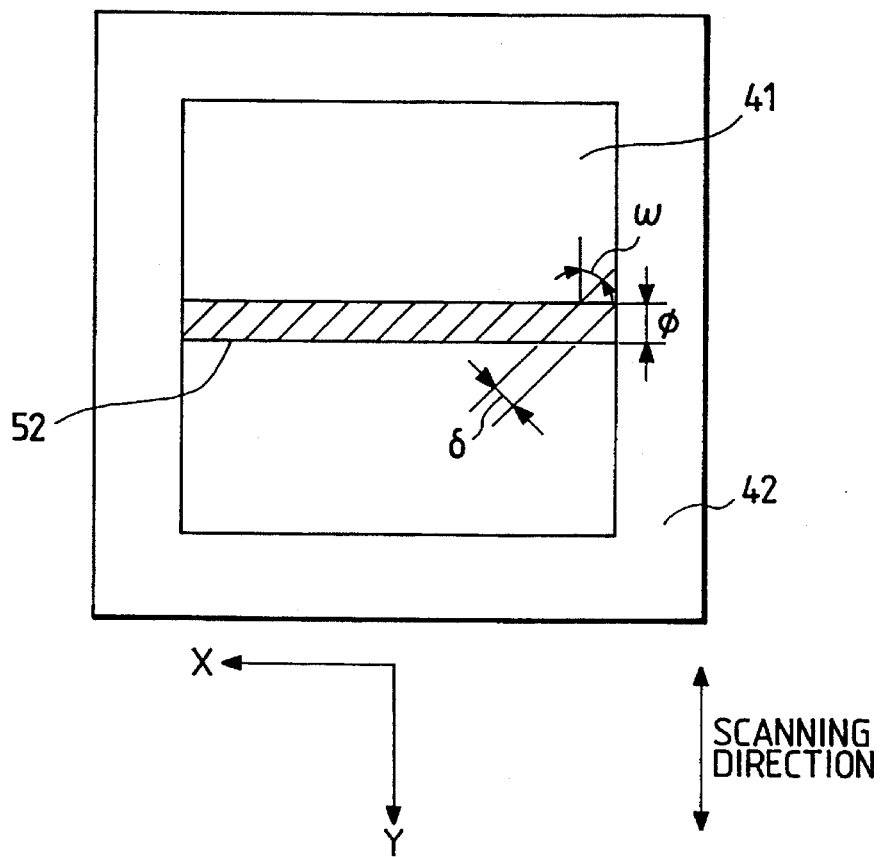
FIG. 13 is a view showing the geometric relationship between a band-shaped radiation region and oblique diffraction fringes.

FIG. 13 shows the geometric relationship between the band-shaped radiation region 52 and oblique diffraction fringes. Note that FIG. 13 also illustrates the pitch δ of the oblique diffraction fringes to be larger than the actual one for the purpose of easy understanding of the drawing. However, in practice, the pitch δ is considerably smaller than a width φ of the band-shaped radiation region.

From a condition that the received light intensity distribution of scattered light from a foreign matter changes by almost one cycle within a predetermined time period t, in other words, from a condition that a scanning distance v·t during the predetermined time period t is equal to the distance between oblique lines of the oblique diffraction fringes in the scanning direction, the following equation (1) can be derived with reference to FIG. 13:

$$\sin \omega = \delta/(v \cdot t) \quad (1)$$

where
- t: the predetermined time period
- ω: the angle of the acute angle defined between the pair of edges 34a and 34b, and a direction transverse to the longitudinal direction of the light beam
- v: the moving speed of an object to be inspected (mask 42 or pellicle 41) relative to a light beam (band-Shaped radiation region 52) to be radiated onto the object to be inspected
- δ: the pitch of oblique diffraction fringes formed on the radiation region 52 upon diffraction by the pair of edges 34a and 34b In this manner, the angle ω of the acute angle defined between the pair of edges 34a and 34b and the direction transverse to the longitudinal direction of the light beam, i.e., the shape of an optimal opening portion of the diaphragm 34 can be calculated.

In this embodiment, the pitch δ of the oblique diffraction fringes is 0.1 mm, the moving speed of the object to be inspected (mask 42 or pellicle 41) relative to the radiation means (31 to 35) is 7 mm/sec, and the predetermined time period t is 0.02 sec. Therefore, in this embodiment, the angle ω of the acute angle defined between the pair of edges 34a and 34b and the direction transverse to the longitudinal direction of the light beam is set to be ω=45.6°.

Note that the moving amount v·t of the surface to be inspected during the predetermined light-receiving time period t of the scattered light is preferably set not to exceed the width φ of the band-shaped radiation region since scattered light from a single foreign matter cannot be received beyond the width φ, in the scanning direction, of the band-shaped radiation region. Therefore, the predetermined light-receiving time period t of scattered light from a foreign matter, the scanning speed v, and the width φ of the band-shaped radiation region 52 preferably satisfy a relation given by the following formula (2):

$$v \cdot t < \phi \quad (2)$$

This embodiment satisfies the above-mentioned formula (2) since the width φ of the band-shaped radiation region is set to be φ=1.5 mm.

In this embodiment, defect inspection may be performed based on a sum total or average of the light intensities sampled at a plurality of timings across the predetermined time period from the instance t0 to the instance t1 in place of the total accumulated light amount.

Figure 14:
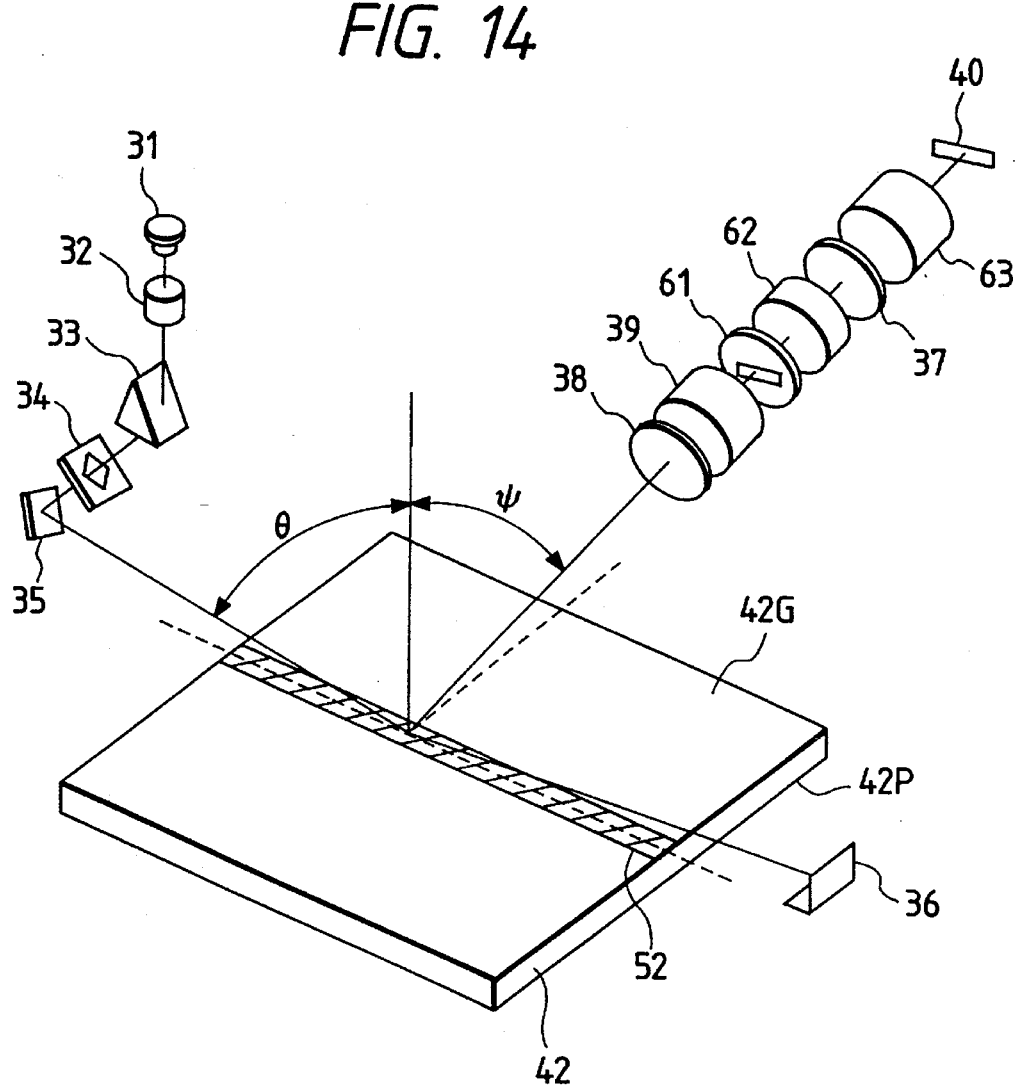
FIG. 14 is a perspective view for explaining the arrangement of a defect inspection apparatus according to still another embodiment of the present invention.

FIG. 14 is a perspective view for explaining the arrangement of a defect inspection apparatus according to still another embodiment of the present invention.

The apparatus of the embodiment shown in FIG. 14 has substantially the same arrangement as that of the apparatus of the embodiment shown in FIG. 10, except for the arrangement of a light-receiving system and an object to be inspected to which this embodiment is applied. The same reference numerals in FIG. 14 denote the same parts as in FIG. 10. The arrangement will be described below while placing an importance on the differences. Note that the processing of the scattered signal is the same as that in the above embodiment, and a repetitive description thereof will be avoided.

Referring to FIG. 14, a laser beam emitted from a semiconductor laser 31 is incident on a glass surface 42G of a mask 42 as a surface to be inspected to have an incident angle θ near 90° via a collimator lens 32, an anamorphic prism 33, a diaphragm 34, and a mirror 35. The mask 42 is supported to extend in a direction almost parallel to the X-Y plane in FIG. 14, and is movable by proper driving means in the Y direction in FIG. 14.

As shown in FIG. 14, the light beam incident on the mask 42 in a direction almost parallel thereto forms a band-shaped radiation region 52 extending along the X direction on the glass surface 42G. On the band-shaped radiation region 52, illuminance nonuniformity due to the influence of diffraction is formed, as shown in FIGS. 11B and 11C, but the light intensity is almost uniform as a whole.

Regularly reflected light from the glass surface 42G of the mask 42 is directly absorbed by a light absorbing member 36. On the other hand, scattered light from a foreign matter on the glass surface 42G is received by a light-receiving system arranged along the Y direction to have a light-receiving angle Ψ near 90°.

In the light-receiving system, a sharp cut filter 38 shields a disturbance light which has a wavelength below that of visible light, and forms noise in a scattered signal. The scattered light passing through the sharp cut filter 38 is focused via a light-receiving lens 39, and passes through a slit 61. The slit 61 is arranged at the imaging position of the light-receiving lens 39, and shields diffracted light from a pattern surface 42P of the mask 42. The scattered light passing through the slit 61 is received by an image sensor 40 via a field lens 62, a soft filter 37, and a condenser lens 63.

The field lens 62 is arranged to prevent scattered light from a foreign matter from being eclipsed. On the image sensor 40, nonsensitive bands are periodically arranged. Therefore, in order to prevent the scattered light from the foreign matter from being imaged on the nonsensitive bands on the image sensor 40 via the light-receiving lens 39, the imaging spot size is increased by the soft filter 37.

As described above, in each of the embodiments shown in FIGS. 10 to 14, since defect inspection is performed based on a scattered signal obtained during a predetermined time period in which the received light intensity distribution from a foreign matter changes by one cycle, radiation light components having almost the same accumulation light amount can be radiated onto foreign matters located at arbitrary positions on the band-shaped radiation region, and scattered light components having almost the same accumulated light amounts can be received. As a result, inspection can be performed for foreign matters located at arbitrary positions on the band-shaped radiation region under substantially the same condition, thus improving the reproducibility, detection rate, and reliability.

As described above, according to the present invention, the radiation region of a light beam on an object to be inspected can be limited to a desired region by the light-shielding means. Furthermore, since the edges of the light-shielding means are formed to cross or traverse the scanning direction of the scanning means, and the object to be inspected is scanned with a light beam having microscopically two-dimensional illuminance nonuniformity, defect detection sensitivity on the entire surface of the object to be inspected can be uniformed.

What is claimed is:

1. A defect inspection apparatus for inspecting a defect on an object to be inspected by radiating a light beam onto the object to be inspected, and receiving scattered light which is generated from the defect upon radiation of the light beam, comprising:

a light source for emitting the light beam;

light beam expansion means for expanding the light beam in a predetermined direction, and radiating the expanded light beam onto the object to be inspected;

scanning means for scanning the object to be inspected relative to the light beam to be radiated onto the object to be inspected in a direction crossing the expansion direction of the light beam;

light-receiving means for photoelectrically converting the scattered light generated from the defect on the object to be inspected; and light-shielding means having a plurality of edges for limiting the light beam expanded by said light beam expansion means at two end portions, in the expansion direction, of the light beam, at least one of said plurality of edges being formed to be transverse to the scanning direction.

2. An apparatus according to claim 1, wherein said plurality of edges comprise a first edge for limiting one end portion, in the expansion direction, of the light beam, and a second edge for limiting the other end portion thereof, and the first and second edges are formed to be substantially parallel to each other.

3. An apparatus according to claim 1, wherein said plurality of edges comprise first and second edges for limiting one end portion, in the expansion direction, of the light beam, and third and fourth edges for limiting the other end portion thereof, the first and second edges are formed to define a predetermined angle therebetween, and the third and fourth edges are formed to define a predetermined angle therebetween.

4. An apparatus according to claim 1, wherein said plurality of edges comprise a first edge for limiting one end portion, in the expansion direction, of the light beam, and a second edge for limiting the other end portion thereof, and the first and second edges are formed to have an arcuated shape.

5. An apparatus according to claim 1, wherein the expanded light beam is radiated downward from an upper position substantially perpendicularly to a surface to be inspected of the object to be inspected.

6. An apparatus according to claim 1, wherein the expanded light beam is radiated from an obliquely upper position substantially parallel to a surface to be inspected of the object to be inspected.

7. An apparatus according to claim 1, wherein said apparatus performs inspection on the object to be inspected on the basis of a received light intensity distribution of the scattered light, which has been detected by said light-receiving means for a predetermined time period.

8. An apparatus according to claim 7, wherein the predetermined time period is a time required for the received light intensity distribution of the scattered light to change by almost one cycle.

9. An apparatus according to claim 7, wherein said apparatus satisfies conditions:

$$\sin \omega = \delta/(v \cdot t)$$

$$v \cdot t < \phi$$

where t: the predetermined time period

ω: an acute angle defined between a pair of edges and a direction transverse to a longitudinal direction of the light beam v: the moving speed of the object to be inspected relative to the light beam radiated onto the object to be inspected $\delta$: pitch of oblique diffraction fringes formed on a radiation region upon diffraction by the pair of edges $\phi$: length, in the scanning direction, of the radiation region.

10. A defect inspection method for inspecting a defect on an object to be inspected by radiating a light beam onto the object to be inspected, and receiving scattered light which is generated from the defect upon radiation of the light beam, comprising steps of:

emitting the light beam;

expanding the light beam in a predetermined direction;

radiating the expanded light beam onto the object to be inspected;

scanning the object to be inspected relative to the light beam to be radiated onto the object to be inspected in a direction crossing the expansion direction of the light beam;

photoelectrically converting the scattered light generated from the defect on the object to be inspected; and limiting said expansion light beam at least at two portions, in the expansion direction, of the light bee by a plurality of edges, wherein at least one of said plurality of edges is formed to be transverse to the scanning direction.

11. A defect inspection method according to claim 10, wherein said plurality of edges comprise a first edge for limiting one end portion, in the expansion direction, of the light beam, and a second edge for limiting another end portion thereof, and the first and second edges are formed to be substantially parallel to each other.

12. A defect inspection method according to claim 10, wherein said plurality of edges comprise first and second edges for limiting one end portion, in the expansion direction, of the light beam, and third and fourth edges for limiting another end portion thereof, the first and second edges are formed to define a predetermined angle therebetween, and the third and fourth edges are formed to define a predetermined angle therebetween.

13. A defect inspection method according to claim 10, wherein the expanded light beam is radiated downward from an upper position substantially perpendicular to a surface to be inspected of the object to be inspected.

14. A defect inspection method according to claim 10, wherein the expanded light beam is radiated from an obliquely upper position substantially parallel to a surface to be inspected of the object to be inspected.

15. A defect inspection method according to claim 10, wherein in said step of photoelectrically converting, the scattered light generated from the defect on the object to be inspected is photoelectrically converted for a predetermined time period.

16. A defect inspection method according to claim 15, wherein said predetermined time period is a time required for the received light intensity distribution of the scattered light to change by almost one cycle.

17. A defect inspection method according to claim 15, wherein said method satisfies conditions:

$$\sin \omega = \delta/(v \cdot t)$$

where t: the predetermined time period $\omega$: an acute angle defined between a pair of said edges and a direction transverse to a longitudinal direction of the light beam v: the moving speed of the object to be inspected relative to the light beam radiated onto the object to be inspected $\delta$: pitch of oblique diffraction fringes formed on a radiation region upon diffraction by the pair of edges $\phi$: length, in the scanning direction, of the radiation region.

* * * * *